United States Patent [19]
Janson et al.

[11] Patent Number: 5,100,399
[45] Date of Patent: Mar. 31, 1992

[54] BABY'S DIAPER OF ADJUSTABLE SIZE

[76] Inventors: Sue Janson, Lockington Road, Bamawm, Victoria; Dana Pendlebury, 1A Coleman Crescent, Rosebud West, Victoria, both of Australia

[21] Appl. No.: 524,143

[22] Filed: May 15, 1990

[30] Foreign Application Priority Data

Dec. 8, 1989 [AU] Australia .................. PJ7782

[51] Int. Cl.$^5$ .................. A61F 13/15; A61F 13/20
[52] U.S. Cl. .................. 604/386; 604/385.1; 604/391
[58] Field of Search .................. 604/385.1, 385.2, 386, 604/387, 389, 390, 391

[56] References Cited

U.S. PATENT DOCUMENTS

| | | | |
|---|---|---|---|
| D. 306,209 | 2/1990 | Coates et al. | D24/50 |
| 2,511,406 | 6/1950 | Israel | 604/386 |
| 3,089,494 | 5/1963 | Schwartz | 604/389 |
| 4,182,336 | 1/1980 | Black | 604/387 |
| 4,536,181 | 8/1985 | Cook | 604/387 |
| 4,936,840 | 6/1990 | Proxmire | 604/385.2 |
| 4,961,736 | 10/1990 | McCloud | 604/385.1 |
| 4,963,140 | 10/1990 | Robertson et al. | 604/389 |
| 4,973,326 | 11/1990 | Wood et al. | 604/391 |

FOREIGN PATENT DOCUMENTS 2322492 11/1974 Fed. Rep. of Germany ...... 604/389

*Primary Examiner*—Randall L. Green
*Assistant Examiner*—Paul Prebilic
*Attorney, Agent, or Firm*—Dilworth & Barrese

[57] ABSTRACT

A baby's diaper comprising a shaped support member (1) of cloth having a modified I-shape with a top end portion (3) having lateral extensions (4 and 5), and a bottom end (6) having shorter and slightly wider lateral extensions (7 and 8), rectangular strips (21, 22 and 23) of VELCRO loop material attached to the outer face of the support member 1 for engagement by strips (15 and 16) of VELCRO hook material attached to the inner face of the support member (1) to secure the diaper in position around a baby; one or more of said spaced strips (21, 22 or 23) being capable of being folded into the diaper to reduce the dimensions of the diaper to enable it to be used with babies of different sizes, and a narrow elongate strip (13) of absorbent cloth attached centrally to the inner face of the support (1) having an extended portion (14) adapted to be folded inwardly onto the support to provide an absorbent pad within the diaper.

3 Claims, 5 Drawing Sheets

BABY'S DIAPER OF ADJUSTABLE SIZE

FIELD OF THE INVENTION

This invention relates to improvements in babies' diapers or other protective device.

BACKGROUND OF THE INVENTION

As the public becomes more conscious of the pollution problems associated with disposable babies' diapers, the need for an easily fitted washable baby's diaper has become more apparent. While a number of fitted babies' diapers have been proposed in the past, a number of problems have been formed to be associated with these diapers.

When a baby is first bore, the size of the diaper required is quite small, but as the baby grows, increasingly larger diapers are required. The presently available fitted diapers are made in a number of graduated sizes which become unusable as the baby outgrows each particular size.

SUMMARY OF THE INVENTION AND OBJECTS

It is therefore one object of the present invention to provide an improved fitted baby's diaper or other protective device which is adjustable to suit the size of the baby.

It is an object of another aspect of the invention to provide a means by which the above difficulty is avoided.

Accordingly, the invention provides a fitted baby's diaper or other protective device comprising a shaped support member having a central strip of absorbent material, said support member terminating in laterally extending end portions which in use partly encircle the waist of the baby when the diaper is attached to the baby, two of said lateral portions at one end of the diaper being provided with attaching means of one type, said diaper being provided with attaching means of another type on the outer surface of the other end of the diaper and to which said attaching means of said one type are in use attached, characterised in that a plurality of discrete portions of attaching means of said other type are secured in spaced relation to the outer surface of said diaper at increasing distances from the edge of said other end of said diaper to enable portions of the diaper to be folded inwardly to reduce the size of the diaper to fit smaller bodies, said folding operation presenting different discrete portions of said attaching means of said other type to said attaching means of said one type to enable the diaper to be secured when folded as defined.

BRIEF DESCRIPTION OF THE DRAWINGS

One preferred embodiment of the invention incorporating each of the above aspects of the invention will now be described with reference to the accompanying drawings in which.

DESCRIPTION OF THE PREFERRED EMBODIMENT

Figure 1:
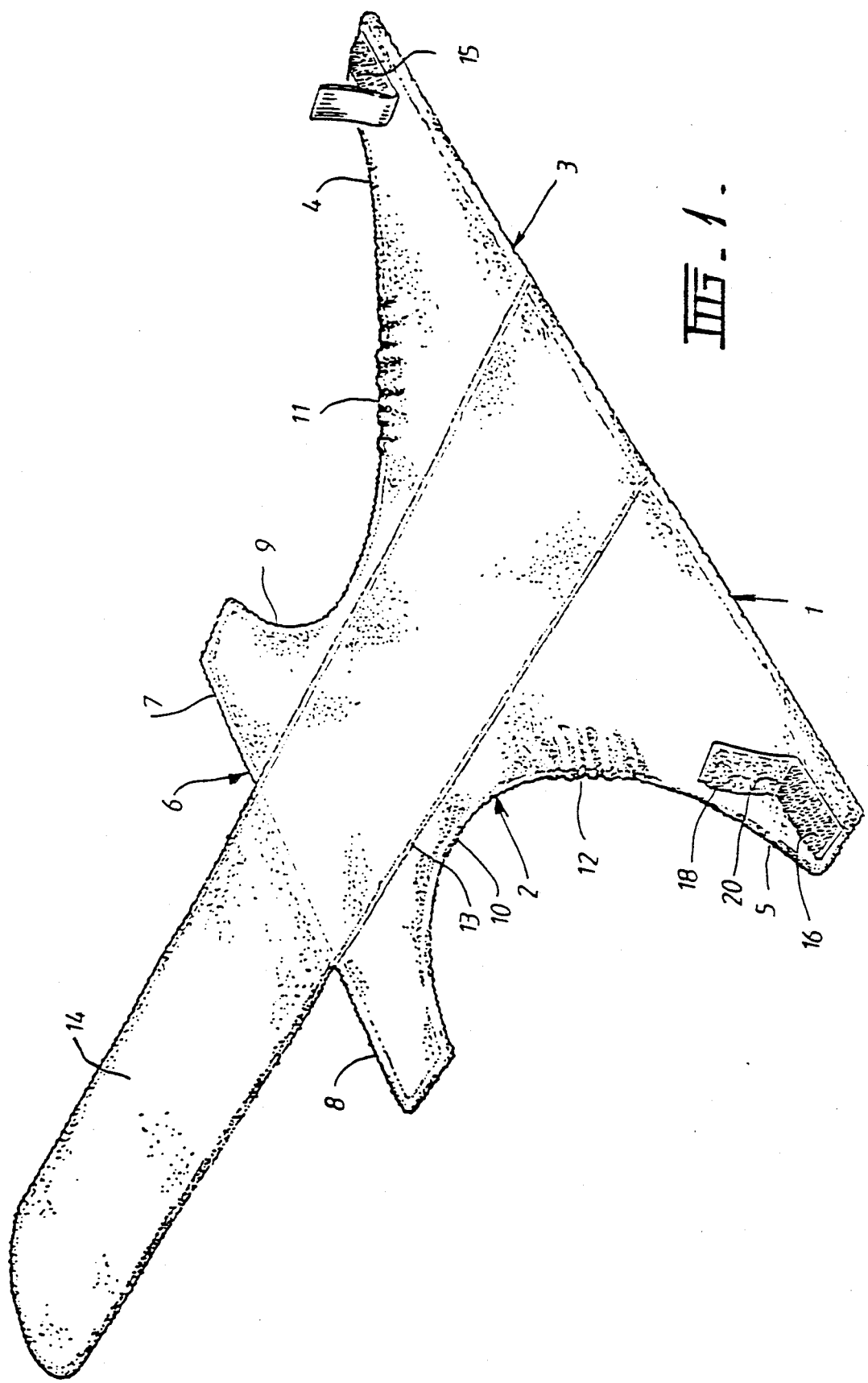
FIG. 1 is a perspective view of the inside face of a diaper embodying the invention.
Figure 2:
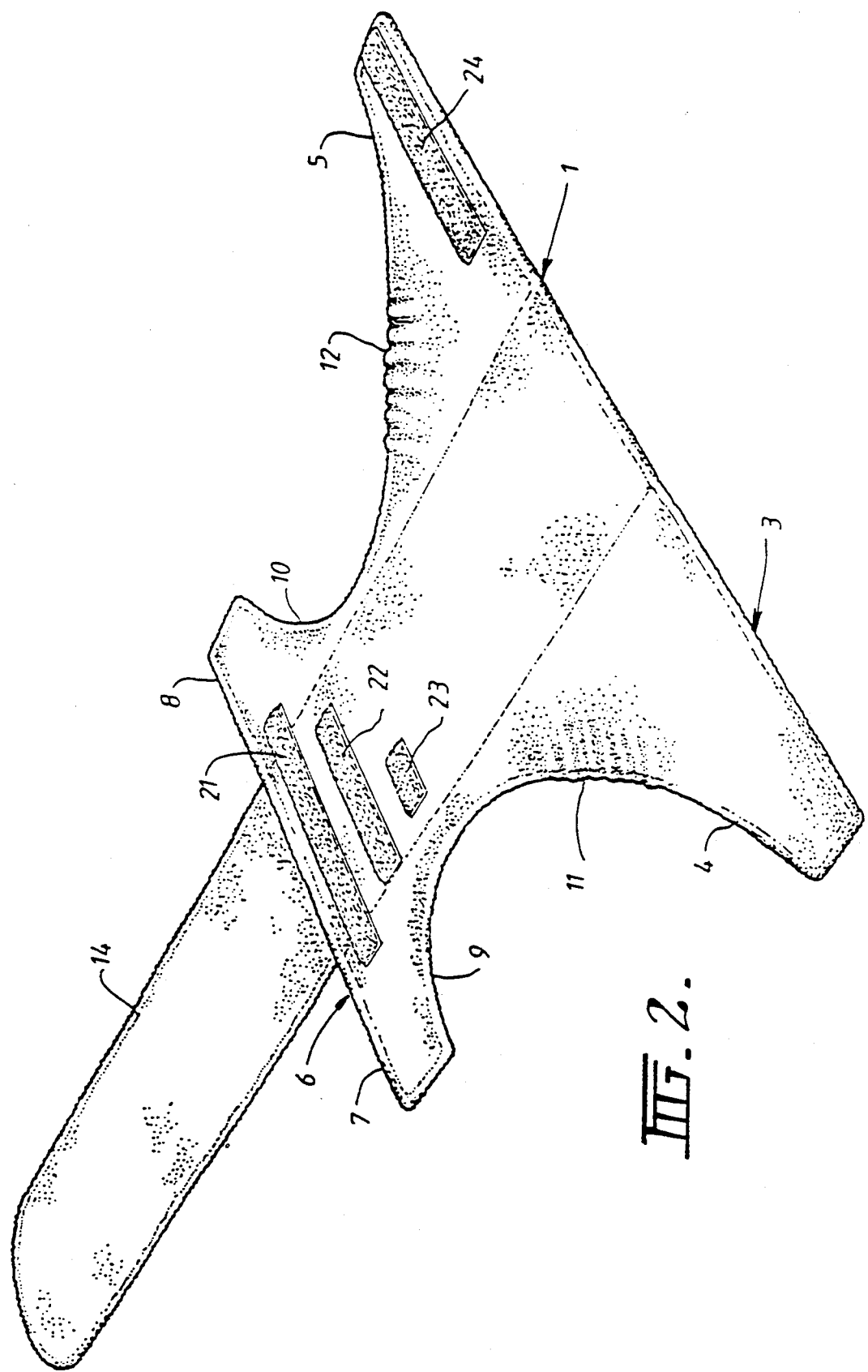
FIG. 2 is a perspective view of the outside face of the diaper of FIG. 1.
Figure 3:
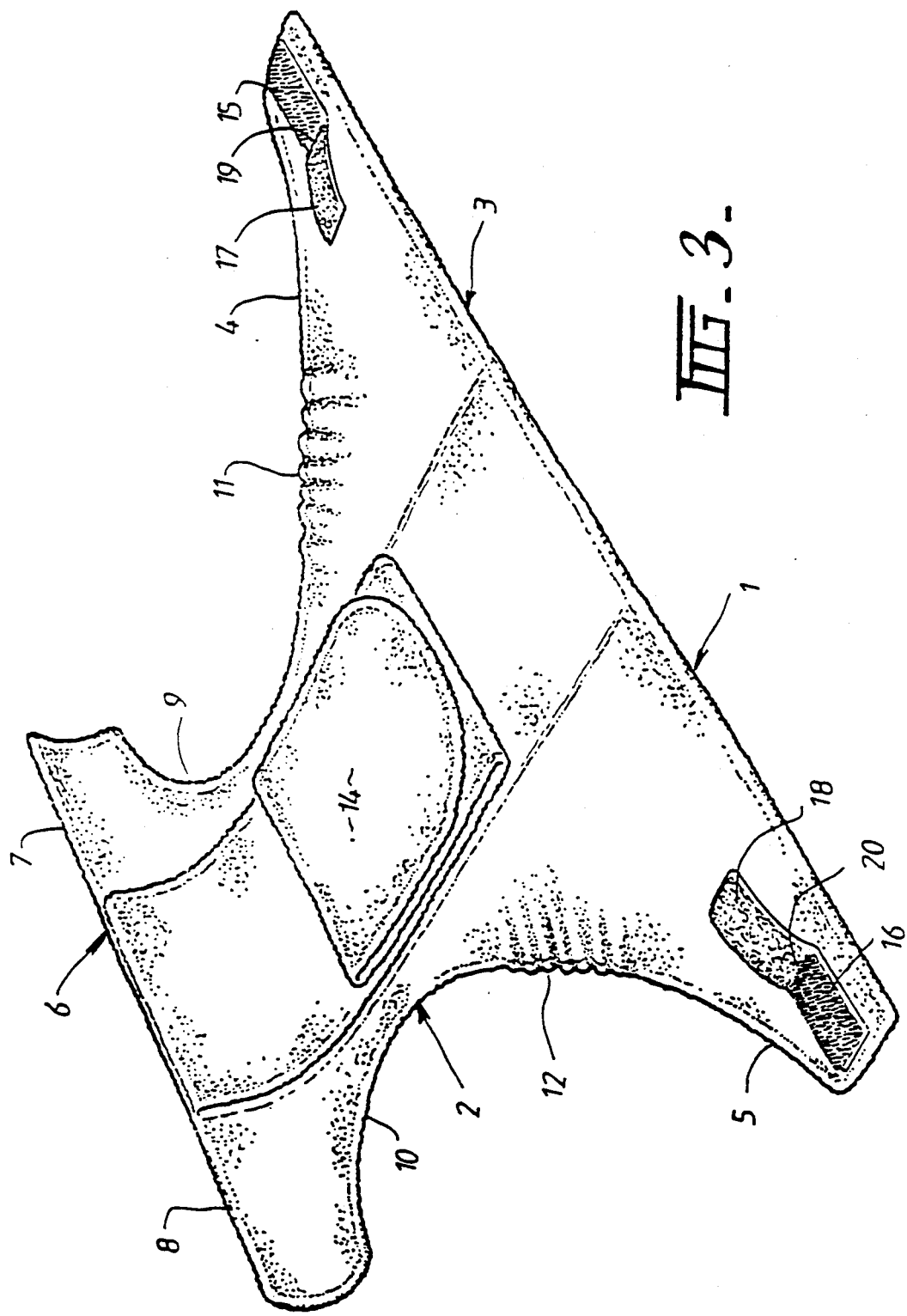
FIG. 3 is a perspective view of the diaper of FIG. 1 ready for fitting to a baby.

With reference to FIGS. 1 to 7 of the drawings, the baby's diaper embodying the invention will be seen to comprise a shaped support member 1 of cloth or other suitable material, which may include a waterproofing material (not shown) of any suitable kind, having a narrow central portion 2, a top end portion 3 having lateral extensions 4 and 5, and a bottom end 6 having shorter and slightly wider lateral extensions 7 and 8 defining a modified I-shaped support. Portions of the shaped side edges 9 and 10 of the support 1 are elasticized at 11 and 12, and a narrow elongate strip 13 of absorbent cloth, such as cotton towelling, is secured centrally to the inner face of the support 1 and has a portion 14 which extends from the bottom end 6 of the support 1 as shown. The portion 14 is adapted to be folded on top of the secured portion of the strip 13 to provide an absorbent pad in the central region of the diaper, as shown in FIG. 3.

Rectangular strips 15 and 16 of velcro (registered trade mark) hood material are secured centrally near the ends of the lateral extensions 4 and 5 to facilitate securement of the diaper to a baby. To protect the hook material strips 15 and 16 against clogging with lint during washing and handling, and to prevent snagging of the hook material strips 15 and 16 with other fabric during washing and drying, tabs 17 and 18 of velcro loop material are attached to the support 1 at 19 and 20. In this way, the tabs 17 and 18 may be folded over and attached to the strips 15 and 16 of hook material to cover the hook material during washing, drying or handling. When the diaper is to be secured, the tabs 17 and 18 are peeled off the hook material strips 15 and 16 to expose the hook material for attachment purposes.

As shown in FIG. 2 of the drawings, three spaced strips 21, 22 and 23 of velcro loop material are attached to the outer face of the support member 1 for engagement with the hook material strip 16 when the diaper is fitted to a baby. To complete the securing operation, a further strip 24 of velcro loop material is attached to the outer face of the support 1 near the top end 3 of the support 1 for engagement by the hook material strip 15 to secure the diaper around the waste of the baby.

Figure 4:
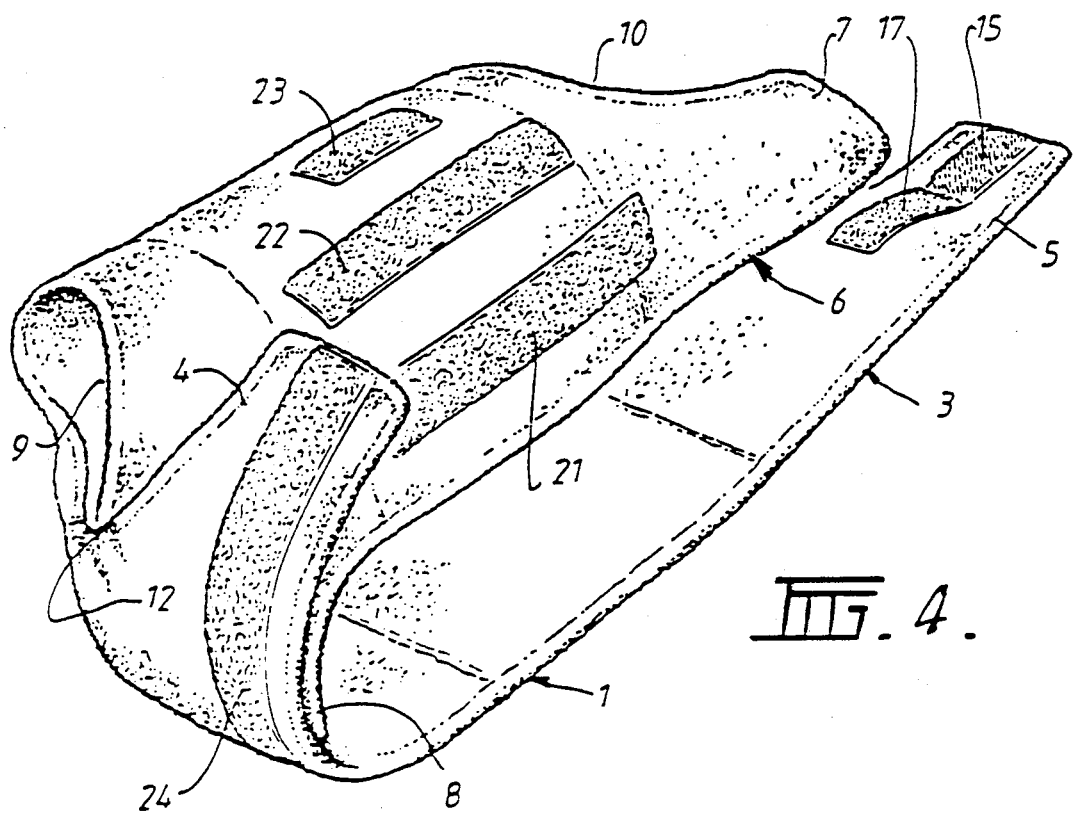
FIGS. 4 and 5 are perspective views of the diaper in the partly and fully fitted positions.
Figure 5:
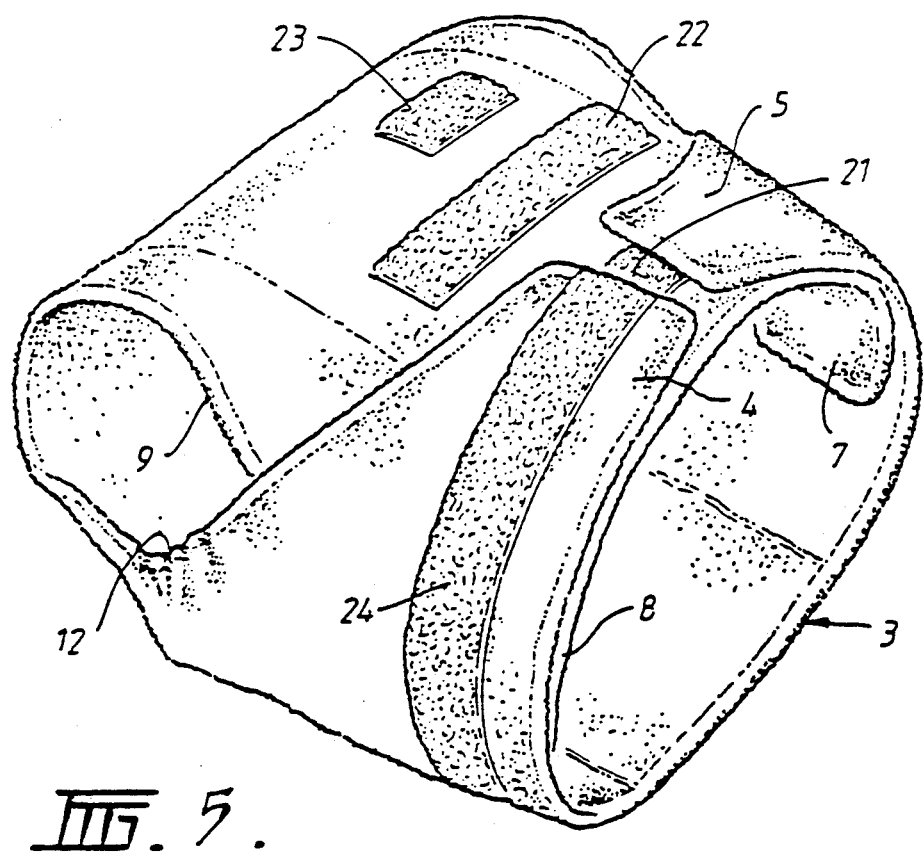
Figure 6:
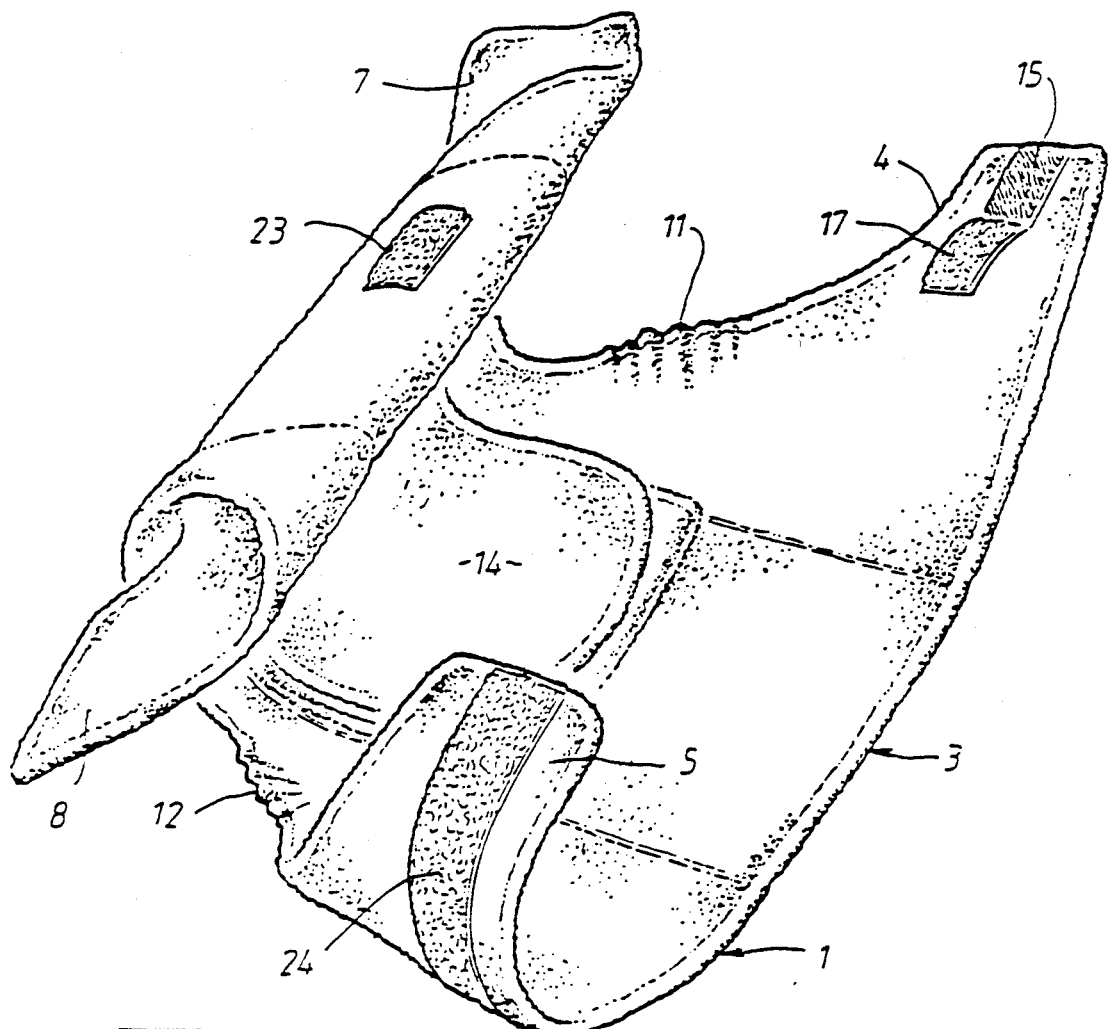
FIGS. 6 and 7 are views similar to FIGS. 4 and 5 showing the diaper folded to fit a new-born baby.
Figure 7:
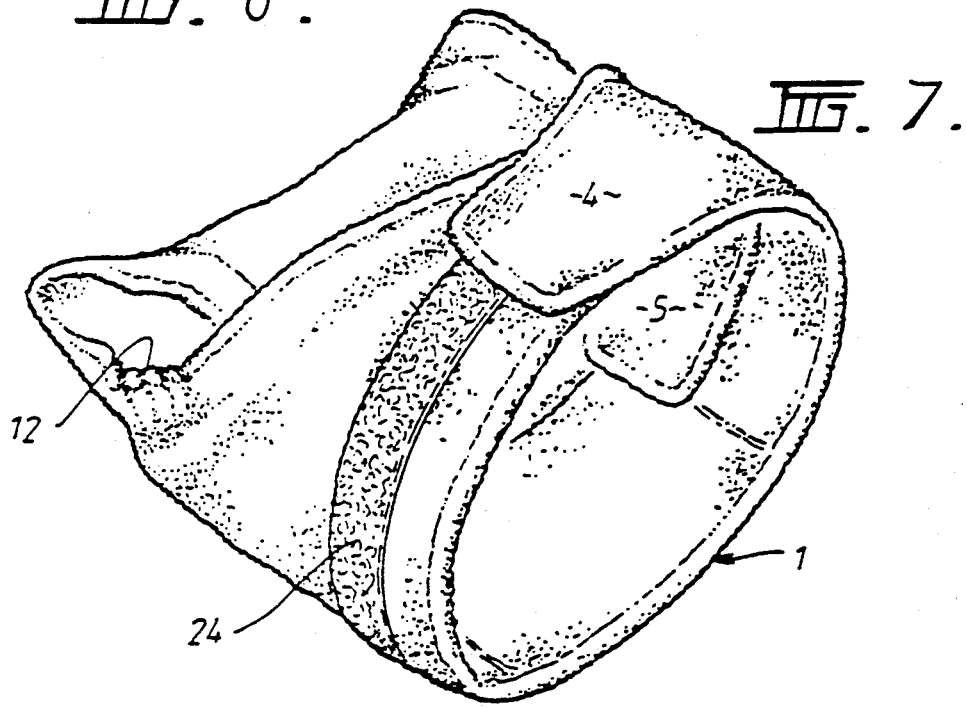

To facilitate fitting of the diaper to new-born babies, the bottom end 6 of the support 1 is folded, as shown in FIG. 6, inwardly to leave only the strip of loop material 23 exposed, following which the end of the strip 14 is folded over the strips 21 and 22 and the hook material strip 16 is attached to the loop strip 23 and the strip 15 attached to the strip 24 to secure the diaper around the waist of the baby, as shown in FIG. 7. For larger babies, only the strip 21 is folded inwardly and the engagement is between the strip 16 and the strip 22. For even larger babies, the engagement is between the strip 16 and the strip 21, as shown in FIGS. 4 and 5. In this way, the diaper embodying the invention will have a longer usable life and need not be replaced as the baby grows.

The provision of spaced discrete strips 21 and 23 of Velcro loop material has the advantage of not only facilitating reduction in the dimensions of the waist of the diaper, but also draws the remaining portions of the diaper upwardly, reducing the depth of the crotch loop when filled to ensure that the sides of the diaper firmly encircle the legs to confine waste products to the diaper in use.

The edges of the support member 1 and the various strips are attached to the support member by sewing, or in any other suitable way.

While the embodiment of the invention has been described in relation to the baby's diaper, it will be appreciated that the invention is equally applicable to other protective devices, such as incontinence devices.

We claim:

1. A fitted protective device such as a baby's diaper, comprising a shaped support member having an inner surface and an outer surface, an elongate strip of absorbent material attached centrally to said support member at a first end and being foldable inwardly over said inner surface of said support member to define an absorbent pad, said support member having first and second ends each terminating in laterally extending end portions which in use partly encircle the waist of a wearer when the support member is attached to the wearer, said lateral end portions at said second end of said support member being provided with hook attaching means, said support member being provided with loop attaching means adapted to be engaged by said hook means on the outer surface of said first end of the support member and to which said hook means are in use secured, a plurality of discrete portions of loop attaching means being secured in spaced relation on said outer surface of said support member at increasing distances from an edge of said first end of said support member whereby portions of said first end of said support member can be folded inwardly to reduce the size of the support member to fit wearers of smaller sizes and to present different ones of said discrete portions to engage said hook attaching means to enable the support member to be secured to the wearer, and a strip of loop attaching means secured to the outer surface of said support member adjacent one side of said second end to enable securement of said hook attaching means thereto when said support member encircles the waist of the wearer whereby different waist sizes may be accommodated by the protective device.

2. A size adjustable diaper having hook and loop fastening means comprising:

a shaped support member having an inner surface and an outer surface and including a longitudinally directed body portion, said support member further having first and second ends terminating in laterally directed wing portions extending substantially perpendicular to said body portion, said first end of said support member having a plurality of strips of laterally extending loop fastening members on said outer surface spaced from each other along said longitudinally directed body portion, said second end of said support member having a strip of hook fastening members on each of said wing portions on said inner surface of said support member, said second end further having at least one strip of loop fastening members on a wing portion on said outer surface thereof, and an elongated strip of absorbent material extending from said first end of said support member, said strip being inwardly foldable to overlay said body portion on said inner surface of said support member, wherein said wing portions of said first and second ends of said support members substantially encircle the waist of a wearer, said hook fastening members of said second end engaging one of said strips of said loop fastening members of said first end to secure said diaper to said wearer, said support member being size adjustable by folding said first end inwardly to overlay said strip to absorbent material and said inner surface to provide for engagement of said hook fastening members with one of said strips to said loop fastening members to secure said diaper to said wearer.

3. A diaper according to claim 2, wherein said strip of loop fastening members on said outer surface of said wing portion of said second end engages a strip of hook fastening members on said inner surface of said wing portion which opposes said strip of loop fastening members to secure said support member about the waist of said wearer.

* * * * *